United States Patent
Schubert et al.

(10) Patent No.: US 10,160,935 B2
(45) Date of Patent: *Dec. 25, 2018

(54) CONSUMER PRODUCTS COMPRISING AMINO MODIFIED HYDROCARBONS

(71) Applicant: The Procter & Gamble Company, Cincinnati, OH (US)

(72) Inventors: Beth Ann Schubert, Maineville, OH (US); Luke Andrew Zannoni, West Chester, OH (US); Robert Joseph McChain, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/000,074

(22) Filed: Jan. 19, 2016

(65) Prior Publication Data
US 2016/0230125 A1    Aug. 11, 2016

Related U.S. Application Data

(60) Provisional application No. 62/112,684, filed on Feb. 6, 2015.

(51) Int. Cl.
| | |
|---|---|
| *A61K 8/49* | (2006.01) |
| *A61K 8/91* | (2006.01) |
| *A61Q 19/00* | (2006.01) |
| *C11D 3/32* | (2006.01) |
| *C11D 3/37* | (2006.01) |
| *C11D 3/30* | (2006.01) |
| *C07D 207/412* | (2006.01) |

(52) U.S. Cl.
CPC .............. *C11D 3/32* (2013.01); *A61K 8/4913* (2013.01); *A61K 8/91* (2013.01); *A61Q 19/00* (2013.01); *C07D 207/412* (2013.01); *C11D 3/30* (2013.01); *C11D 3/37* (2013.01); *C11D 3/3788* (2013.01)

(58) Field of Classification Search
CPC combination set(s) only.
See application file for complete search history.

(56) References Cited

U.S. PATENT DOCUMENTS

| | | | |
|---|---|---|---|
| 3,113,026 A | 12/1963 | Sprung et al. | |
| 4,612,132 A | 9/1986 | Wollenberg et al. | |
| 2004/0048765 A1 | 3/2004 | Cooney et al. | |
| 2005/0202980 A1* | 9/2005 | Loper | C10L 1/221 508/232 |
| 2008/0199420 A1 | 8/2008 | Wendel et al. | |
| 2008/0214718 A1* | 9/2008 | DiStefano | B82Y 30/00 524/432 |
| 2010/0161029 A1 | 6/2010 | Philippini et al. | |
| 2012/0266837 A1 | 10/2012 | Barton | |
| 2013/0059927 A1 | 3/2013 | Boeckh et al. | |

FOREIGN PATENT DOCUMENTS

WO    WO 2006050968    5/2006

OTHER PUBLICATIONS

U.S. Appl. No. 15/000,078, filed Jan. 2016, Schubert et al.*
Pathmamanoharan, C. "Preparation of Monodisperse Polyisobutene Grafted Silica Dispersion" Colloids Surf. 1988, 34, 81-88.*
C. Pathmamanoharan: "Preparation of monodisperse polyisobutene grafted silica dispersion", Colloids and Surfaces, vol. 34, No. 1, Jan. 1, 1988, pp. 81-88, XP055267961, NL, ISSN: 0166-6622.
International Search Report and Written Opinion dated Apr. 4, 2016, U.S. Appl. No. 15/000,074, 14 pgs.
International Search Report and Written Opinion dated Mar. 15, 2016, U.S. Appl. No. 15/000,0748, 15 pgs.
Database Registry (Online), Chemical Abstracts Service, Columbus Ohio, Mar. 12, 2012, Chemical Catalogue Supplier: Ukrorgsyntez Ltd.: "1,2-Ethanediamine, N1, N1-dimethyl-N2-[2-(3-propyl-1-pyrrolidinyl)ethyl]-", XP002755473, retrieved from STN, Database accession No. 1566930-95-7, abstract.
Database Registry (Online), Chemical Abstracts Service, Columbus Ohio, Mar. 12, 2012, Chemical Catalogue Supplier: Ukrorgsyntez Ltd.: "1,3-Propanediamine, N3-[2-(3-ethyl-1-pyrrolidinyl)ethyl]-N1,N1-dimethyl-(CA Index Name)", XP002755474, retrieved from STN, database accession No. 1565102-46-6, abstract.

* cited by examiner

*Primary Examiner* — Amanda L Aguirre
(74) *Attorney, Agent, or Firm* — Jason J Camp

(57) ABSTRACT

Products selected from the group consisting of: hair conditioners, fabric softeners, skin moisturizers, shampoos, paper product additives, cosmetics, personal cleansing products, shave preparation products, detergents, non-woven additives, oral care products, and assembled products comprising treated paper or non-woven components, and comprising a polyisobutylene composition.

2 Claims, No Drawings

CONSUMER PRODUCTS COMPRISING AMINO MODIFIED HYDROCARBONS

FIELD OF THE INVENTION

The invention relates to consumer products comprising modified hydrocarbon compounds. The invention relates particularly to consumer products comprising modified polyisobutylene compounds for formulated products.

BACKGROUND OF THE INVENTION

Formulated consumer products are well known in the art. Products such as cosmetics, shampoos and conditioners for hair care, soaps and detergents may benefit from the presence of an oil or other lubricant providing a particular tactile sensation during application and use. The tactile sensation may be accomplished via the presence of hydrocarbon compositions or silicone materials. Market volatility, which may induce undesirable levels of price fluctuation in the costs of basic compositions associated with imparting the targeted tactile sensation to the product and its use, leads to a desire for alternative compositions capable of providing the desired consumer benefit and experience in terms of product feel, appearance and performance.

SUMMARY OF THE INVENTION

In one aspect, the Invention comprises a formulated product selected from the group consisting of: hair conditioners, fabric softeners, skin moisturizers, shave preparation products, shampoos, paper product additives, cosmetics, and oral care products, and comprising a chemical composition comprising compounds selected from the group consisting of: compounds having the formula:

R-C-Z-W wherein R comprises a hydrocarbon, C comprises a cyclic connector; Z comprises an amine; and W comprises a functional group, wherein functional group W is substantially free of oxygen in the instance where the cyclic connector, C, further comprises a carbonyl group.

DETAILED DESCRIPTION OF THE INVENTION

While the specification concludes with claims particularly pointing and distinctly claiming the invention, it is believed the present invention will be better understood from the following description.

All percentages herein are by weight of the compositions unless otherwise indicated.

All ratios are weight ratios unless otherwise indicated.

All percentages, ratios, and levels of ingredients referred to herein are based on the actual amount of the ingredient by weight, and do not include solvents, fillers, or other materials with which the ingredient may be combined as commercially available products, unless otherwise indicated.

As used herein, "comprising" means that other steps and other ingredients which do not affect the end result can be added. This term encompasses the terms "consisting of" and "consisting essentially of".

All cited references are incorporated herein by reference in their entireties. Citation of any reference is not an admission regarding any determination as to its availability as prior art to the claimed invention.

Unsaturated hydrocarbons may be modified via the ene reaction of maleic anhydride to form succinic anhydrides, which may subsequently be modified via reaction with an amine under acidic conditions to yield imide amines and their derivatives. For example, polyisobutylene (PIB), may be modified via the ene reaction of maleic anhydride to form PIB succinic anhydride (PIBSA). The PIBSA may subsequently be modified via reaction with an amine under acidic conditions to yield a PIB imide amine. That product may be subjected to a lithium aluminum hydride (LAH) reduction to yield a cyclic PIB triamine of the general formula:

R-C-Z-W

Where R comprises a hydrocarbon such as PIB; C comprises a cyclic connector such as pyrrolidine; Z comprises an amine and W comprises a functional group associated with the relevant amine. Functional groups W comprising a carbonyl are substantially free of oxygen.

In one embodiment, Z comprises a monoamine, and W comprises dimethyl nitrogen, or the cyclic amine PIB-triamine. In one embodiment, Z comprises a diamine and W comprises a hydrocarbon (eg: PIB) plus a cyclic connector (eg: pyrrolidine), or the cyclic amine-di-PIB triamine. The cyclic amines described above may be further reacted with ethyl bromide to yield PIB ethyl triquat, and di-PIB ethyl triquat, respectively.

Further examples of functional groups W include, without being limiting: dialkylamino groups including but not limited to dimethylamino, diethylamino, dipropyl, diisopropyl, dibutyl, dihexyl, dioctyl, dodecyl, didodecyl, dihexadecyl, disoctadecyl, dilauryl, dicoconut, ditallow, or dioleyl. Functional groups may also comprise trialkyl ammonium groups, including but not limited to trimethyl ammonium, dimethylethyl ammonium, dimethylbutyl ammonium, dimethylhexyl ammonium, dimethyloctyl ammonium, dimethyldecyl ammonium, dimethyldodecyl ammonium, dimethylhexadecyl ammonium, dimethyloctadecyl ammonium. Those of skill in the art will appreciate that when the functional group comprises a quaternary nitrogen, a suitable charge balancing anion or anions will also be present. Functional groups may also comprise a cyclic connector and hydrocarbon.

Cyclic connectors include, but are not limited to, pyrrolidine, succinimide, piperidine, glutarimide, hexamethyleneimine, isoindole, phthalimide, pyromellitic diimide, octahydro-1H-indole, aza-cyclooctane, aza-cyclononane, and bicyclics such as bicyclo[2.2.2]octane-2,3-dicarboxylic imide.

In one embodiment, PIB succinic anhydride (PIBSA) may be reacted with a single primary amine under acidic conditions to form a mono-PIB imide diamine. The imide amines may be quatted directly to form imide alkyl quat/amines. Exemplary forms of the mono-PIBSI alkyl quat/amines may be produced using each of: ethyl bromide, octyl bromide, dodecyl bromide, and hexadecyl bromide.

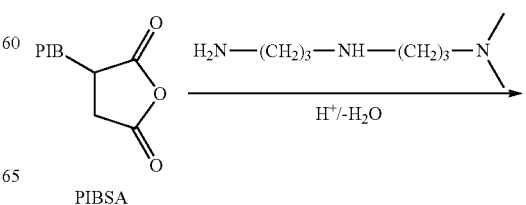

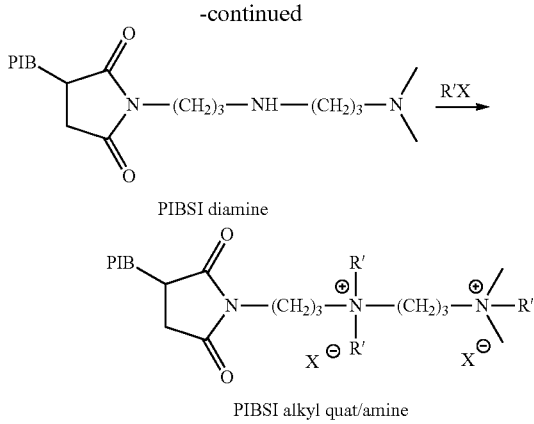

PIBSI diamine

PIBSI alkyl quat/amine

In one embodiment, PIB succinic anhydride (PIBSA) may be reacted with a double primary amine under acidic conditions to form a di-PIB imide diamine. The imide amines may be quatted directly to form imide alkyl quat/amines. Exemplary forms of the di-PIBSI alkyl quat/amines may be produced using each of: ethyl bromide, dodecyl bromide, and stearyl bromide.

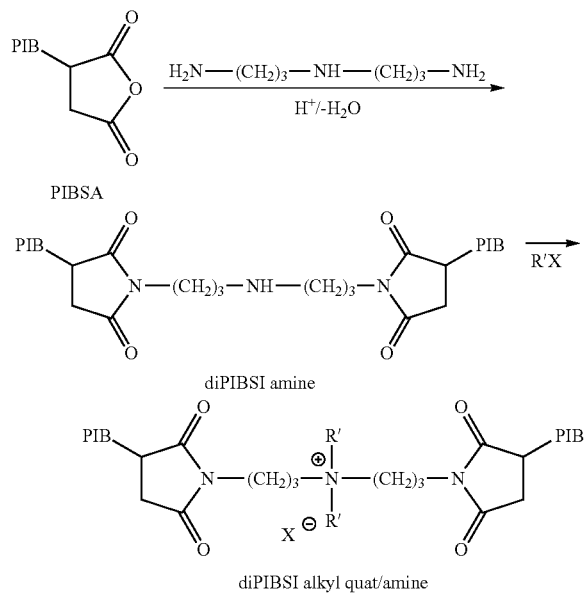

PIBSA diPIBSI amine diPIBSI alkyl quat/amine

A polyisobutylene with average molecular weight of approximately 1000 (PIB 1000) may be utilized in the preparation of the exemplary compounds described above. Hydrocarbons having an average molecular weight of between about 500 Amu and about 8500 Amu may be utilized in the preparation of the different compositions set forth above.

The prepared composition may be incorporated into formulated products to impart particular product lubricity and to enhance the conditioning properties of the product with respect to the target object of the products intended use. Exemplary products include: hair care products such as shampoos, conditioners, and styling products; skin care products such as moisturizers, shave preparation products, cleansers and cosmetics; fabric care products such as detergents and fabric softeners, paper sizing and conditioning products, and oral care products. paper product additives, personal cleansing products, non-woven additives, and assembled products comprising treated paper or non-woven components.

EXAMPLES

Example 1

Emulsification and Intrinsic Performance

The modified PIB materials described above may be dissolved in an equal weight of hexanes (15 g). Tergitol NP-40 my be dissolved in deionized water to a concentration of 20 wt % and added to a stainless steel beaker (11.5 to 15.0 g active Tergitol NP-40 added). The modified PIB/hexane solution may be added dropwise into the aqueous NP-40 solution while mixing with a benchtop homogenizer (IKA Ultra Turrax or similar) at 17,500 RPM or higher depending on the quality of mixing. Once all of the PIB/Hexane material is added, the emulsion may be heated to remove the hexanes. Final % solids of the resulting emulsion may be measured using a Mettler-Toledo Moisture Balance.

The emulsions may be diluted with deionized water to a concentration of approximately 0.16 wt % active modified PIB and directly deposited onto cotton fabric (100% Mercerized Combed Cotton Warp Sateen Fabric, approximately 155 grams/square meter, Style #479 available from Test Fabrics, West Pittston Pa. desized using standard procedures before use) at 3 mg active/g substrate. All treated substrates may be dried and allowed to equilibrate for at least 16 hours before technical testing in a controlled temperature-controlled humidity room. The secant modulus of the fabric may be measured via an Instron stretch-recovery hysteresis test, where the secant modulus of the fabric is measured after 4 hysteresis cycles. The data are reported in Table 1 as % reduction in secant modulus versus a water control.

Reduction in Secant Modulus

Reduction in Secant Modulus (RSM) is a measure of the compositions' capacity to impart softness to a treated fabric. Without being bound by theory it is believed that a lower secant modulus correlates with a more flexible fabric which will be perceived as softer by consumers. Note that RSM is reported as a reduction in secant modulus versus a control, so that a higher reported value correlates with a lower secant modulus and a superior softness result.

The RSM measurement is performed using a commercial tensile tester with computer interface for controlling the test speed and other test parameters, and for collecting, calculating and reporting the data. RSM testing may be run using an Instron 5544 Testing System running the Bluehill software package. The test is conducted in a room or chamber with air temperature controlled to 20-25° C. and Relative Humidity (RH) controlled to 50%. All fabrics used in the test are equilibrated in the temperature and humidity condition of the test location for at least 16 hrs prior to collecting measurements.

During testing, the load cell is chosen so that the tensile response from the sample tested will be between 10% and 90% of the capacity of the load cells or the load range used. Typically a 500N load cell is used for woven fabrics. The grips are selected such that they are wide enough to fit the fabric specimen and minimize fabric slippage during the test. Typically pneumatic grips set to 60 psi pressure and fitted with 25.4 mm-square crosshatched faces are used. The instrument is calibrated according to the manufacturer's instructions. The grip faces are aligned and the gauge length is set to 25.4 mm (or 1 inch). The fabric specimen is loaded into the pneumatic grips such that the warp direction is parallel to the direction of crosshead motion. Sufficient tension is applied to the fabric strip to eliminate observable slack, but such that the load cell reading does not exceed 0.5N. The specimens are tested with a multi-step protocol as follows:

(Step 1) Go to a strain of 10% at a constant rate of 50 mm/min and then return to 0% strain at a constant rate of 50 mm/min. This is the first hysteresis cycle.

(Step 2) Hold at 0% strain for 15 seconds and re-clamp the specimen to eliminate any observable slack and maintain a 25.4 mm gauge length without letting the load cell reading exceed 0.5N (Step 3) Go to a strain of 10% at a constant rate of 50 mm/min and then return to 0% strain at a constant rate of 50 mm/min. This is the second hysteresis cycle.

(Step 4) Hold at 0% strain for 15 seconds and re-clamp the sample to eliminate any observable slack and maintain a 25.4 mm gauge length without letting the load cell reading exceed 0.5N (Step 5) Go to a strain of 10% at a constant rate of 50 mm/min and then return to 0% strain at a constant rate of 50 mm/min. This is the third hysteresis cycle.

(Step 6) Hold at 0% strain for 15 seconds and re-clamp the sample to eliminate any observable slack and maintain a 25.4 mm gauge length without letting the load cell reading exceed 0.5N (Step 7) Go to a strain of 10% at a constant rate of 50 mm/min and then return to 0% strain at a constant rate of 50 mm/min. This is the fourth hysteresis cycle.

(Step 8, optional) Hold at 0% strain for 15 seconds and re-clamp the sample to eliminate any observable slack and maintain a 25.4 mm gauge length without letting the load cell reading exceed 0.5N (Step 9, optional) Go to a strain of 10% at a constant rate of 50 mm/min and then return to 0% strain at a constant rate of 50 mm/min. This is the fifth hysteresis cycle.

(Step 10, optional) Hold at 0% strain for 15 seconds and re-clamp the sample to eliminate any observable slack and maintain a 25.4 mm gauge length without letting the load cell reading exceed 0.5N (Step 11, optional) Go to a strain of 10% at a constant rate of 50 mm/min and then return to 0% strain at a constant rate of 50 mm/min. This is the sixth hysteresis cycle.

The resulting tensile force-displacement data from the fourth hysteresis cycle (step 7) are converted to stress-strain curves using the initial sample dimensions, from which the secant modulus used herein, is derived. The initial sample dimensions are 25.4 mm width×25.4 mm length×0.41 mm thickness. A fourth cycle secant modulus at 10% strain is defined as the slope of the line that intersects the stress-strain curve at 0% and 10% strain for this fourth hysteresis cycle. A minimum of three fabric specimens are measured for each fabric treatment, and the resulting fourth cycle secant moduli are averaged to yield an average fourth cycle secant modulus at 10%. The intrinsic performance of compositions of the present invention are compared by calculating the percentage to which a given composition reduces the fourth cycle secant modulus at 10% strain compared to a control fabric specimen treated with water.

The reported value for average percent RSM is calculated as:

$$100\% \times \frac{(\text{4th cycle secant modulus})_{CONTROL} - (\text{4th cycle secant modulus})_{TEST\ LEG}}{(\text{4th cycle secant modulus})_{CONTROL}}$$

TABLE 1

| Ingredient | A | B | C | D | E | F | G | H | I | J | K | L | M |
|---|---|---|---|---|---|---|---|---|---|---|---|---|---|
| Tergitol NP-40 [1] | 15.0 | 15.0 | 11.5 | 15.0 | 11.5 | 15.0 | 15.0 | 11.5 | 11.5 | 11.5 | 15.0 | 15.0 | 15.0 |
| PIB 1000 [2] | 15.0 | | | | | | | | | | | | |
| PIB succinic anhydride [3] | | 15.0 | | | | | | | | | | | |
| PIB triamine(Ex. 3) | | | 15.0 | | | | | | | | | | |
| diPIB triamine(Ex. 4) | | | | 15.0 | | | | | | | | | |
| PIB ethyl triquat(Ex. 5A) | | | | | 15.0 | | | | | | | | |
| diPIB ethyl triquat (Ex. 5B) | | | | | | 15.0 | | | | | | | |
| PIBSI C2 quat/amine (Ex. 6A) | | | | | | | 15.0 | | | | | | |
| PIBSI C8 quat/amine (Ex 6B) | | | | | | | | 15.0 | | | | | |
| PIBSI C12 quat/amine (Ex 6C) | | | | | | | | | 15.0 | | | | |
| PIBSI C16 quat/amine (Ex 6D) | | | | | | | | | | 15.0 | | | |
| diPIBSI C2 quat/amine (Ex 7A) | | | | | | | | | | | 15.0 | | |
| diPIBSI C12 quat/amine (Ex 7B) | | | | | | | | | | | | 15.0 | |
| diPIBSI C18 quat/amine (Ex 7C) | | | | | | | | | | | | | 15.0 |
| Water | to 100% | to 100% | to 100% | to 100% | to 100% | to 100% | to 100% | to 100% | to 100% | to 100% | to 100% | to 100% | to 100% |
| % Reduction in Secant modulus on 479 Fabric, 3 mg modified PIB/g fabric | 14 | 32 | 55 | 45 | 36 | 37 | 29 | 41 | 49 | 47 | 32 | 36 | 42 |

[1] 70% aqueous solution of nonylphenol ethoxylate surfactant available from Sigma-Aldrich
[2] Polyisobutylene of molecular weight approximately 1000 g/mol, such as Glissopal 1000 available from BASF or Rewopal PIB 1000 available from Evonik.
[3] Available as Glissopal ™ SA from BASF.

Example 2

Rinse-Added Fabric Care Compositions

Without being bound by theory, it is believed that both fabric extraction energy and fabric friction are technical measures of fabric softness. In this example, terry fabrics may be run-through an automatic mini-washer with the compositions of Table 2 in the rinse-cycle.

The fabric used in the miniwasher is a white terry cloth hand towel, manufactured by Standard Textile. The brand name is Euro Touch and is composed of 100% cotton. Fabrics are cut in half to yield a weight of 50-60 grams and desized using standard procedures. Four hand towel halves may be combined with additional 100% cotton ballast to yield a total fabric weight of 250-300 grams per miniwasher. Fabrics may be first washed with a 5.84 g dose of Tide Free & Gentle laundry detergent in 2 gal of 6 GPG (GPG=hardness grains per gallon) water. During the rinse cycle, 2.4 g of the rinse added fabric treatment may be added. Upon completion of the rinse and spin cycles, fabrics may be tumble dried. A set of control fabrics may be prepared, washed with a 5.84 g dose of Tide Free & Gentle laundry detergent in 2 gal of 6 GPG (GPG=hardness grains per gallon) water where no rinse added fabric treatment is added. Upon completion of the rinse and spin cycles, fabrics may be tumble dried. For each treatment including the control fabrics, a total of three wash-rinse-dry cycles may be completed.

Extraction Energy Reduction

Extraction energy is measured using a Phabrometer Fabric Evaluation System, manufactured by Nu Cybertek, Inc, Davis, Calif. Treated fabrics are cut into 11 cm diameter circles and equilibrated in a constant temperature (CT) room for 24 hours before measuring. The CT room temperature is 20-25 deg. C. with a relative humidity of 50%. A fabric circle is placed between 2 rings. The top ring is weighted and can be varied based on fabric type. A small probe pushes the fabric through the hole in the ring (perpendicular to the fabric surface). The instrument records the force (as voltage) needed to push the fabric through the ring as a function of time. Between each fabric measurement, the bottom of the weight, the inside of the ring, and the base in which the ring is sitting are cleaned with an alcohol wipe having 70% isopropyl alcohol and 30% deionized water. Alcohol wipes may be purchased from VWR International. All raw data is exported to Microsoft Excel. There are 108 data points in each exported curve, but only the first 85 are used. Each curve is integrated from 1 to 85 and the sum is reported as the unitless "Extraction Energy". For each test treatment a minimum of 8 fabric circles are evaluated (two circles from each of four terry cloths) and a sample Standard Deviation is calculated. "Extraction Energy Reduction" (EER) is obtained by subtracting the average extraction energy of the fabric samples treated with test legs in the table below from the average extraction energy of the control sample. Without being bound by theory, a higher EER indicates more softening performance.

Kinetic Coefficient of Friction

For friction measurements, when drying of the fabrics is completed, all fabric cloths are equilibrated for a minimum of 8 hours at 20-25 deg. C. and 50% Relative Humidity. Treated and equilibrated fabrics are measured within 2 days of treatment. Treated fabrics are laid flat and stacked no more than 10 cloths high while equilibrating. Friction measurements are all conducted under the same environmental conditions used during the conditioning/equilibration step.

A Thwing-Albert FP2250 Friction/Peel Tester with a 2 kilogram force load cell is used to measure fabric to fabric friction. (Thwing Albert Instrument Company, West Berlin, N.J.). The sled is a clamping style sled with a 6.4 by 6.4 cm footprint and weighs 200 grams (Thwing Albert Model Number 00225-218). The distance between the load cell to the sled is set at 10.2 cm. The crosshead arm height to the sample stage is adjusted to 25 mm (measured from the bottom of the cross arm to the top of the stage) to ensure that the sled remains parallel to and in contact with the fabric during the measurement. The 11.4 cm×6.4 cm cut fabric piece is attached to the clamping sled so that the face of the fabric on the sled is pulled across the face of the fabric on the sample plate. The sled is placed on the fabric and attached to the load cell. The crosshead is moved until the load cell registers between ~1.0-2.0 gf. Then, it is moved back until the load reads 0.0 gf. At this point the measurement is made and the Kinetic Coefficient of Friction (kCOF) recorded. For each treatment, at least four replicate fabrics are measured and the results averaged.

The emulsions from Example 1 may be formulated into rinse-added fabric enhancer compositions according to the Table 2:

TABLE 2

| Ingredient | A | B | C | D | E | F | G | H | I | J | K |
|---|---|---|---|---|---|---|---|---|---|---|---|
| Fabric Softener Active[1] | 11.0 | 11.0 | 9.0 | 11.0 | 11.0 | 9.0 | 11.0 | 11.0 | 11.0 | 11.0 | 11.0 |
| Perfume | 1.5 | 1.5 | 1.5 | 1.5 | 1.5 | 1.5 | 1.5 | 1.5 | 1.5 | 1.5 | 1.5 |
| Perfume microcapsule[2] | 0.33 | 0.33 | 0.33 | 0.33 | 0.33 | 0.33 | 0.33 | 0.33 | 0.33 | 0.33 | 0.33 |
| Quaternized polyacrylamide[3] | 0.2 | 0.2 | 0.2 | 0.2 | 0.2 | 0.2 | 0.2 | 0.2 | 0.2 | 0.2 | 0.2 |
| Calcium chloride | 0.15 | 0.15 | 0.15 | 0.15 | 0.15 | 0.15 | 0.15 | 0.15 | 0.15 | 0.15 | 0.15 |
| Water soluble dialkyl quat[4] | 1.0 | 1.0 | 1.0 | 1.0 | 1.0 | 1.0 | 1.0 | 0.25 | 0.25 | 0.25 | 0.25 |
| PIBSA | 3.0 | | | | | | | | | | |
| PIB triamine (Example 1.C) | | 5.0 | 5.0 | 3.0 | | | | | | | |
| PIB ethyl triquat (Example 1.E) | | | | | 3.0 | 5.0 | | | | | |
| diPIB ethyl triquat (Example 1.F) | | | | | | | 3.0 | | | | |
| diPIB triamine | | | | | | | | 3.0 | | | |

TABLE 2-continued

| Ingredient | A | B | C | D | E | F | G | H | I | J | K |
|---|---|---|---|---|---|---|---|---|---|---|---|
| (Example 1.D) PIBSI C8 quat/amine (Example 1.H) | | | | | | | | | 3.0 | | |
| PIBSI C12 quat/amine (Example 1.I) | | | | | | | | | | 3.0 | |
| PIBSI C16 quat/amine (Example 1.J) | | | | | | | | | | | 3.0 |
| Water, suds suppressor, stabilizers, pH control agents, buffers, dyes & other optional ingredients | to 100% pH = 3.0 | to 100% pH = 3.0 | to 100% pH = 3.0 | to 100% pH = 3.0 | to 100% pH = 3.0 | to 100% pH = 3.0 | to 100% pH = 3.0 | to 100% pH = 3.0 | to 100% pH = 3.0 | to 100% pH = 3.0 | to 100% pH = 3.0 |
| Kinetic Coefficient of Friction[6] | 1.22 | 1.03 | 1.11 | 1.01 | 1.03 | 1.04 | 1.08 | 1.12 | 1.03 | 1.06 | 1.03 |
| Extraction Energy Reduction | 4.2 | 6.7 | 3.4 | 7.07 | 6.9 | 5.0 | 6.5 | 6.0 | 7.2 | 6.4 | 5.4 |

[1] N,N di(tallowoyloxethyl) - N,N dimethylammonium chloride available from Evonik Corporation, Hopewell, VA.
[2] Available from Appleton Paper of Appleton, WI
[3] Cationic polyacrylamide polymer such as a copolymer of acrylamide/[2-(acryloylamino)ethyl]tri-methylammonium chloride (quaternized dimethyl aminoethyl acrylate) available from BASF, AG, Ludwigshafen under the trade name Sedipur 544.
[4] Didecyl dimethyl ammonium chloride under the trade name Bardac ® 2280 available from Lonza or Hydrogenated tallowallcyl(2-ethylhexyl)dimethyl ammonium methylsulfate fromAkzoNobel under the trade name Arquad ® HTL8-MS
[5] Available as Glissopal™ SA from BASF.
[6] The kinetic coefficient of friction for fabrics with no rinse added fabric softener is 1.51

Exemplary amino-modified hydrocarbons of the invention include compounds having formulas of:

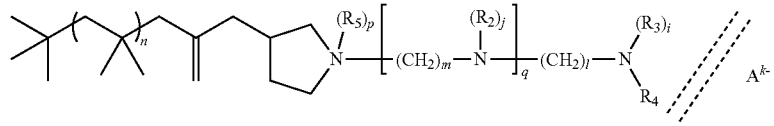

Wherein:
l, m=1-6, independently
j=1-2
i=1-2
p=0-1
q=0-6
$R_2$, $R_3$, $R_4$, $R_5$=H, Hydrocarbon, independently
$k \leq q(j-1)+p+(i-1)$

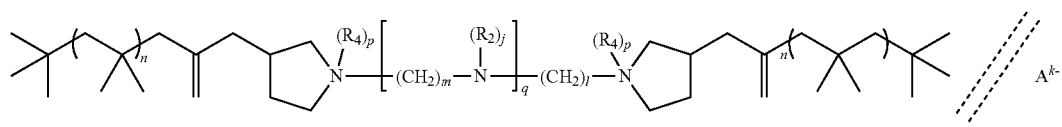

Wherein:
l, m=1-6, independently
j=1-2
p=0-1
q=0-6
$R_2$, $R_4$=H, Hydrocarbon, independently
$k \leq q(j-1)+2p$

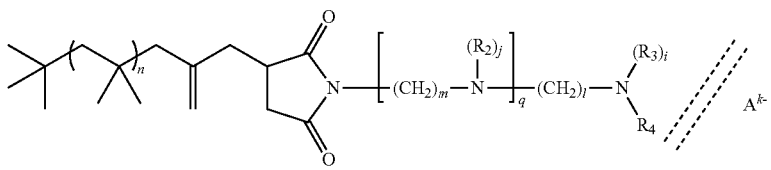

Wherein:
l, m=1-6, independently
j=1-2
i=1-2
q=0-6
$R_2$, $R_3$, $R_4$=H, Hydrocarbon, independently
k≤q(j−1)+(i−1)

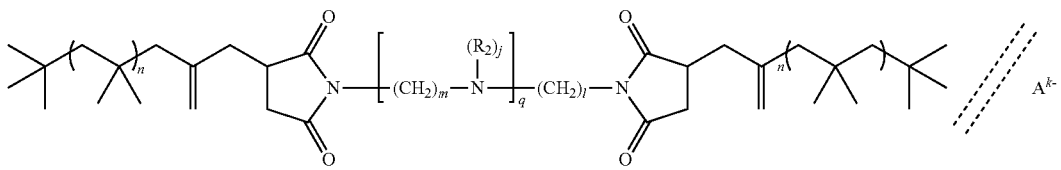

Wherein:
l, m=1-6, independently
j=1-2
q=0-6
$R_2$=H, Hydrocarbon, independently
k≤q(j−1)

$A^{k-}$ is a suitable charge balancing anion or anions such that the total charge, k, of the charge-balancing anion or anions is equal to and opposite from the net charge on the compound.

In one embodiment, $A^{k-}$ is Cl−, Br−, I−, methylsulfate, toluene sulfonate, carboxylate, phosphate or combinations thereof.

Example 3—Synthesis of Mono-Polyisobutylene Triamine (PIB Triamine)

388.35 g of polyisobutylene succinic anhydride [PIBSA, FA07-002SA, BASF] is dissolved in 1 L of toluene in a 2 L, 3-neck round-bottomed flask. The flask is equipped with an overhead stirrer, Dean-Stark trap, and Claisen adaptor with thermocouple and slow addition funnel 36.958 g of N,N-dimethyldipropylenetriamine [10563-29-8] (Aldrich) is dissolved in 40 mL of toluene. in a separate Erlenmeyer flask. This solution is transferred to a slow addition funnel and slowly added to the PIBSA solution at room temperature with an exotherm to 35° C. The slow addition funnel is rinsed with ~60 mL of toluene into the reaction flask. Methane sulfonic acid (3.2 mL, [75-75-2], Aldrich) is then added to the reaction flask via the slow addition funnel, followed by a 120 mL toluene rinse, and replacement with only a thermocouple.

The reaction is brought to reflux, collecting toluene/water for ~5 hours. After allowing the reaction to cool to room temperature, it is worked up by extracting 3× with saturated sodium carbonate using saturated sodium chloride to break the formed emulsion. Emulsion is back extracted with toluene. Toluene layers are combined, dried over magnesium sulfate, and rotary evaporated yielding 390.10 g polyisobutylene succinimide (PIBSI) diamine. H-1 NMR in $C_6D_6$ confirms imide methylene (δ=3.6 ppm) as well as removal of methane sulfonic acid; C-13 confirms methylene/methyl carbons adjacent to nitrogen (δ=45.5, 47.2, 48.4 ppm).

380.90 g of PIBSI diamine is dissolved in ~1 L of toluene in a 5 L, 3-neck round-bottomed flask. The flask is equipped with an overhead stirrer, a thermocouple, and a Claisen adaptor with slow addition funnel and argon purge. To the slow addition funnel is added 69 mL of lithium aluminum hydride [16853-85-3] (Aldrich, 2.0 M LAH in THF). Reaction flask is cooled in an ice bath to 0.5° C. before slowly adding LAH solution dropwise with an exotherm to 6.1° C. The process is repeated twice more with 2×100 mL portions of 2.0 M LAH solution (269 mL total). Total addition time is over 3 hours, then the reaction is allowed to warm to room temperature overnight. IR confirms disappearance of carbonyl stretches prior to workup.

PIB triamine is worked up by cooling the flask in an ice bath followed by slow addition of 20.4 mL of water with rapid overhead stirring to yield a highly viscous heterogeneous mixture. To this mixture is added 20.4 mL of 15% sodium hydroxide in water, then 61.2 mL of water. Salts are allowed to precipitate overnight as flask is warmed back to room temperature. Solution is filtered, solvent is removed via rotary evaporation, and material is dried in vacuum oven at 80° C. overnight to yield 299.64 g of PIB triamine C-13 NMR in $C_6D_6$ and IR confirms disappearance of carbonyl resonances; H-1 NMR confirms disappearance of imide methylene (δ=3.6 ppm).

Example 4—Synthesis of Di-Polyisobutylene Triamine (diPIB Triamine)

389.0 g of polyisobutylene succinic anhydride [PIBSA, Glissopal™ SA, BASF] is dissolved in 1 L of toluene in a 2 L, 3-neck round-bottomed flask. The flask is equipped with an overhead stirrer, Dean-Stark trap, and Claisen adaptor with thermocouple and slow addition funnel. 19.548 g of bis(3-aminopropyl) amine [56-18-8] (Aldrich) is dissolved in 75 mL of toluene in a separate Erlenmeyer flask. This solution is transferred to a slow addition funnel and is added slowly to the PIBSA solution at 20.3° C. with an exotherm to 33.8° C. The slow addition funnel is rinsed with ~75 mL of toluene into the reaction flask.

Dowex 50W8, 50-100 Mesh; ion exchange resin [1119-78-8] (Acros Organics) is rinsed with toluene and 20 mL (toluene wet) resin is added to the reaction flask. The flask is then brought to reflux, collecting water/toluene until the toluene phase is clear. The reaction is then cooled, the resin is removed by filtration, and is rotary evaporated yielding 407.82 g of di-polyisobutylene succinimide (di-PIBSI) amine. H-1 NMR in $C_6D_6$ confirms imide methylenes ($\delta$=3.7 ppm); C-13 confirms methylene carbons adjacent to nitrogen ($\delta$=46.9 ppm).

389.71 g of diPIBSI amine is dissolved in ~1 L of toluene in a 5 L, 3-neck round-bottomed flask, The flask is equipped with an overhead stirrer, a thermocouple, and a Claisen adaptor with slow addition funnel and argon purge. To the slow addition funnel is added 88 mL of lithium aluminum hydride [16853-85-3] (Aldrich, 2.0 M LAH in THF). The reaction flask is cooled in ice bath to 1.5° C. before slowly adding LAH solution dropwise with very little exotherm. The process is repeated twice more with 2×100 mL portions of 2.0 M LAH solution (288 mL total). Total addition time is over 3 hours, then allowed to warm to room temperature overnight. IR confirmed disappearance of carbonyl stretches prior to workup.

diPIB triamine is worked up by cooling flask in ice bath followed by slow addition of 21.8 mL of water with rapid overhead stirring to yield a highly viscous heterogeneous mixture. To this mixture is added 21.8 mL of 15% sodium hydroxide in water, then 65.4 mL of water. Salts are allowed to precipitate overnight as flask is warmed back to room temperature. Solution is filtered and solvent is removed via rotary evaporation to yield 331.27 g of diPIB triamine C-13 NMR in $C_6D_6$ and IR confirms disappearance of carbonyl resonances; H-1 NMR confirms disappearance of imide methylene ($\delta$=3.7 ppm).

Example 5—Synthesis of Polyisobutylene Ethyl Triquat (PIB Triquat) and Di-Polyisobutylene Ethyl Triquat (diPiB Triquat)

| Example | Triamine | Sodium bicarbonate | Ethyl bromide | Final Product |
|---|---|---|---|---|
| 5.A | 30.41 g PIB triamine (Example 3) | 1.8327 g | 26.1 mL | 27.09 g PIB triquat |
| 5.B | 27.89 g diPIB triamine (Example 4) | 0.8990 g | 12.6 mL | 28.75 g diPIB triquat |

Triamine is dissolved in ~100 g of THF in a round-bottomed flask with stir bar and septum. Sodium bicarbonate [144-55-8] (EMD) and ethyl bromide [74-96-4] (Aldrich) are added with gas evolution observed via an attached bubbler. Reaction is stirred for several days until gas evolution ceases. Salts are removed via filtration. Excess ethyl bromide is removed via rotary evaporation. Materials are placed in vacuum overnight at ~60° C.

Example 6—Synthesis of Mono-Polyisobutylene Alkyl Quat/Amines (PIBSI Alkyl Quat/Amines)

| Ex. | PIBSI diamine (Example 3) | Sodium bicarbonate | Solvent | Alkylating agent | Final Product |
|---|---|---|---|---|---|
| 6.A | 30.1 g | 1.3745 g | THF | 15 mL ethyl bromide [74-96-4] | 30.32 g PIBSI C2 quat/amine |
| 6.B | 20.20 g | 1.6463 g | Toluene | 8.9450 g 1-bromooctane [111-83-1] | 21.53 g PIBSI C8 quat/amine* |
| 6.C | 22.84 g | 1.8393 g | Toluene | 13.2963 g 1-bromododecane [143-15-7] | 29.39 g PIBSI C12 quat/amine |
| 6.D | 22.04 g | 1.7616 g | Toluene | 15.2671 g 1-bromohexadecane [112-82-3] | 30.54 g PIBSI C16 quat/amine |

*Some material lost during workup.

PIBSI diamine from Example 3 is dissolved in THF or toluene in a round-bottomed flask with stir bar and septum. Sodium bicarbonate [144-55-8] (EMD) and alkylating agent (Aldrich) are added with gas evolution observed via an attached bubbler. For ethyl bromide, reaction is stirred for several days at room temperature until gas evolution ceases. For all other alkylating agents, solutions are brought to a reflux overnight. Salts are removed via filtration. Excess alkylating agent is removed via rotary evaporation, then Kugelrohr, until the alkylating agent is no longer visible in the H-1 NMR ran in $C_6D_6$ (triplet at $\delta$=~3 ppm).

Example 7—Synthesis of diPIBSI Alkyl Quat/Amines

| Ex. | diPIBSI amine (Example 4) | Sodium bicarbonate | Alkylating agent | Final Product |
|---|---|---|---|---|
| 7.A | 30.64 g | 0.8086 g | 5.5 mL ethyl bromide [74-96-4] | 29.06 g diPIBSI C2 quat/amine |
| 7.B | 14.32 g | 0.3513 g | 9.7918 g 1-bromododecane [143-15-7] | 4.24 g diPIBSI C12 quat/amine |
| 7.C | 14.13 g | 0.3480 g | 10.9885 g 1-bromooctadecane [112-89-0] | 10.95 g diPIBSI C18 quat/amine | diPIBSI amine from Example 4 is dissolved in THF in a round-bottomed flask with stir bar and septum, sodium bicarbonate [144-55-8] (EMD) and alkylating agent (Aldrich) are added with gas evolution observed via an attached bubbler. For ethyl bromide, reaction is stirred at 38-40° C. for several days, then salts are removed via filtration, solvent is removed, and material is dried in a vacuum oven at 60° C. overnight. For all other alkylating agents, solutions are heated at 55° C. overnight. Salts are removed via filtration, then rotary evaporated to concentrate, precipitated into isopropanol, and dried in a vacuum oven at 60° C. over a weekend.

The PiBSA starting material used in generating the materials of the present invention may include any of a number of impurities. One such impurity might be the bi-cyclic variant of the PiBSA material, which may be depicted as:

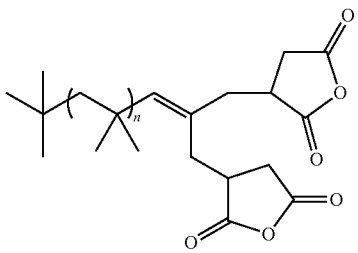

Those of skill in the art will appreciate that the further functionalization and/or modifications of the succinic anhydride moiety of the PiBSA starting material, to yield the materials of the present invention, might result in similar functionalization and/or modification of both succinic anhydride moieties of the bi-cyclic variant depicted above, thereby resulting in similarly functionalized impurities in the R-C-Z-W materials of the present invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A formulated consumer product comprising compounds selected from the group consisting of chemical compounds having the structure:

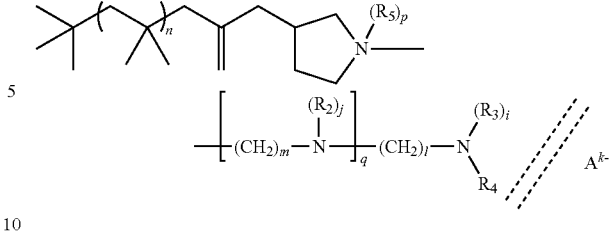

wherein:
l, m=1-6, independently
j=1-2
i=1-2
p=0-1
q=0-6
$R_2$, $R_3$, $R_4$, $R_5$=H, Hydrocarbon, independently
k≤q(j−1)+p+(i−1); or

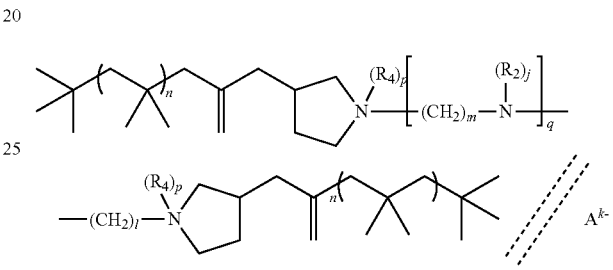

wherein:
l, m=1-6, independently
j=1-2
p=0-1
q=0-6
$R_2$, $R_4$=H, Hydrocarbon, independently
k≤q(j−1)+2p;
wherein $A^{k-}$ is a suitable charge balancing anion or anions such that the total charge, k, of the charge-balancing anion or anions is equal to and opposite from the net charge on the compound,
and combinations thereof.

2. The consumer product according to claim 1 wherein the product is selected from the group consisting of: hair conditioners, fabric softeners, skin moisturizers, shampoos, paper product additives, cosmetics, personal cleansing products, shave preparation products, detergents, non-woven additives, oral care products, and assembled products comprising treated paper or non-woven components.

* * * * *